Figure 1:
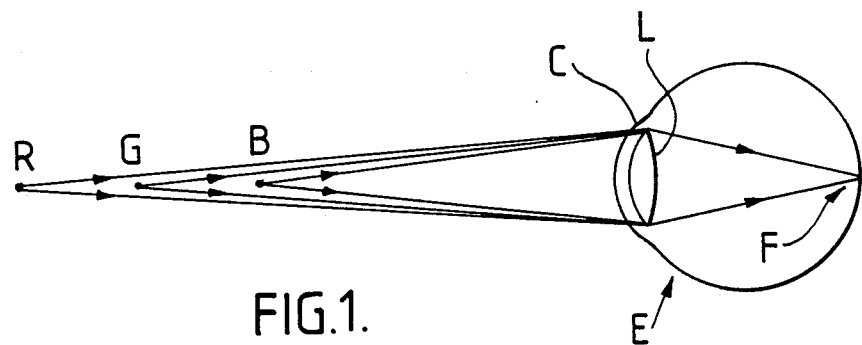

United States Patent [19]

Freeman

[11] Patent Number: 4,641,934

[45] Date of Patent: Feb. 10, 1987

[54] OPHTHALMIC LENS WITH DIFFRACTIVE POWER

[75] Inventor: Michael H. Freeman, Clwyd, United Kingdom

[73] Assignee: Pilkington P.E. Limited, United Kingdom

[21] Appl. No.: 533,993

[22] Filed: Sep. 20, 1983

Related U.S. Application Data

[63] Continuation-in-part of Ser. No. 368,362, Apr. 14, 1982.

[30] Foreign Application Priority Data

Sep. 29, 1982 [GB] United Kingdom ............... 8227818

[51] Int. Cl.⁴ .................... G02C 7/02; G02C 7/04; G02B 5/32; A61F 2/16
[52] U.S. Cl. .................... 351/159; 350/3.72; 350/162.16; 350/168; 350/437; 351/160 R; 351/161; 623/6
[58] Field of Search .......... 351/159, 160 R–162, 351/163, 168; 350/168, 437, 3.72, 162.16; 623/6

[56] References Cited

U.S. PATENT DOCUMENTS

| | | | |
|---|---|---|---|
| 3,004,570 | 10/1961 | Ruhle | 350/452 |
| 3,339,997 | 9/1967 | Wesley | 351/161 |
| 3,794,414 | 2/1974 | Wesley | 351/161 |
| 4,073,579 | 2/1978 | Deeg et al. | 351/169 |
| 4,162,122 | 7/1979 | Cohen | 351/161 |
| 4,206,518 | 6/1980 | Jardon et al. | 623/6 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,377,329 | 3/1983 | Poler | 351/160 R |
| 4,402,579 | 9/1983 | Poler | 351/160 R |

OTHER PUBLICATIONS

"The Leiske Physioflex Style 10 Anterior Chamber Lens: Surgide, Jan. 4, 1981, No. 3–31.

Primary Examiner—John K. Corbin
Assistant Examiner—Scott J. Sugarman
Attorney, Agent, or Firm—F. Eugene Davis, IV; Mark P. Stone

[57] ABSTRACT

An ophthalmic lens incorporates a transmission hologram which has negative diffractive power and introduces positive longitudinal chromatic aberration to add to the natural longitudinal chromatic aberration of the human eye, thereby reducing the need to accommodate. The lens also has refractive power to balance the diffractive power or to give a desired overall or residual power.

18 Claims, 2 Drawing Figures

OPHTHALMIC LENS WITH DIFFRACTIVE POWER

RELATED APPLICATIONS

This application is a continuation-in-part of my earlier application Ser. No. 368,362 filed on Apr. 14, 1982 entitled ARTIFICIAL EYE LENSES.

This invention concerns improvements in or relating to ophthalmic lenses, including in particular contact lenses and spectacle lenses.

The human eye is known to exhibit longitudinal chromatic aberration so that objects at the same distance but of different colours cannot all be sharply focussed at the same time. Thus, to effect simultaneous sharp focussing orange and red objects need to be placed farther away than a green object while blue and violet objects have to be nearer the eye than the green object. The extent of the effect is about one dioptre and there is evidence to suggest that the eye/brain system makes use of this to avoid refocussing, concentrating on the blue components of objects that are close and on the red components for distant vision.

According to the present invention there is provided an ophthalmic lens having negative diffractive power which introduces positive longitudinal chromatic aberration. Such introduced positive longitudinal chromatic aberration adds to the natural longitudinal chromatic aberration of the eye and hence increases the range of the chromatic effect. This can enable the eye/brain system to perform a wider variety of tasks without need to adjust the eye focus (accommodate) by concentrating on the appropriate colour component at the different respective distances. If the extent of positive longitudinal chromatic aberration required to be introduced by the ophthalmic lens is D dioptres, then the diffractive power of the lens is preferably about −3.4D dioptres; for example if the required extent of the introduced aberration is +1 dioptre (to give, with the eye's natural extent of +1 dioptre, a total range of +2 dioptres), then the diffractive power of the lens may be about −3.4 dioptres.

The ophthalmic lens preferably has refractive power so that the overall, or residual, power of the lens is determined by the algebraic sum of the diffractive and refractive powers. If desired, the refractive power may be positive and of a magnitude such as to balance, or cancel, the diffractive power so that the overall or residual power is substantially zero. For example, where the lens has a diffractive power of about −3.4 dioptres it may have a refractive power of about +3.4 dioptres so that there is no substantial residual power. Alternatively, however, the relative values of the diffractive and refractive powers may be such as to provide the lens with an overall or residual power, for example to give a required corrective power for the particular eye with which the ophthalmic lens is to be used. Thus, the refractive power may be positive and of greater magnitude than the diffractive power to give a positive residual power, or may be positive but of smaller magnitude than the diffractive power to give a negative residual power, or may be negative to give a greater negative overall power.

The refractive power is preferably provided by faces which are curved as viewed in axial-section, and which may be of spherical curvature.

The diffractive power is preferably provided by a transmission hologram. The hologram may be optically generated in a surface layer of the lens or within the bulk material of the lens, or may be mechanically generated as a surface relief hologram on the lens or within the lens. The diffractive power may be provided over the full visually used area of the lens, or may be provided over part only of that area. The lens may be a contact lens which may have the diffractive power over its full visually used area. Alternatively, the lens may be a spectacle lens which may have the diffractive power over part only of the visually used area, e.g. over a part corresponding to the near or reading portion of a bifocal or progressive spectacle lens. As a further possibility the lens could be an implant lens in which case the diffractive power is preferably provided over the full visually used area of the lens.

The efficiency of diffraction is preferably more than 50% at all wavelengths across the visible spectrum and the maximum efficiency is preferably more than 70%. The difference between the maximum and minimum efficiencies across the visible spectrum is preferably less than 20%, e.g. if the maximum efficiency is nearly 100% then the minimum efficiency is preferably more than 80%.

Figure 2:
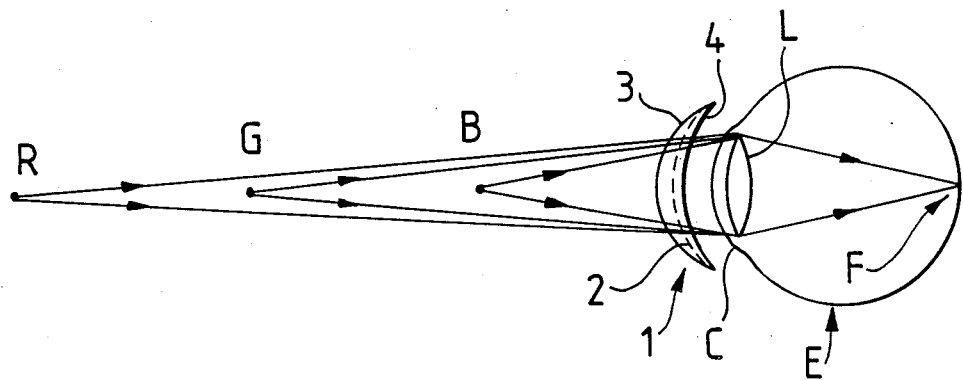

In order that the invention may be better understood, reference will now be made to the accompanying drawing in which:

FIG. 1 is a schematic (and not to scale) representation of the chromatic viewing properties of a normal human eye, FIG. 2 is a schematic (and not to scale) representation similar to FIG. 1 but with an ophthalmic lens in accordance with the invention associated with the eye.

Referring to FIG. 1, the normal human eye E has a cornea C and natural lens L by which light is focussed at F to form an image on the retina. Objects at different distances are viewed by adjusting the shape of the natural lens L (through the action of the eye muscles) so as to alter its focal length to achieve focussing at the point F of light from the respective object distance. This property of the eye is commonly known as "accommodation". However, the eye exhibits longitudinal chromatic aberration, which means that with the eye lens L at any one accommodation setting different colours from the same distance are not all focussed at the same point. This arises because the media of the eye have refractive indices which are slightly greater at the blue end of the spectrum than at the red end. Conversely, therefore, at any one accommodation setting, the eye can sharply focus on to the retina the image of a blue object at one distance and the image of a red object at a greater distance. This is illustrated in FIG. 1 which shows a blue object B nearer the eye and a red object R further from the eye, from both of which light is sharply focussed on the retina at F with the lens L at the same accommodation setting. Between the blue and red objects there is shown a green object G (wavelength 555 nm) whose image is also sharply focussed on to the retina at F at that particular accommodation setting. It will be understood that the distance variation is continuous through the visible spectrum and that blue, green and red objects are given as illustrative.

As a particular example of the variation at a specific accommodation setting, if in FIG. 1 the green object G is at a distance of one meter from the eye E and the eye lens L is in a state of accommodation such that (in conjunction with the action of the cornea C) an image of the green object G is sharply focussed on the retina at F, then the red object R would need to be at a distance of 2 meters from the eye E, and the blue object B would have to be at a distance of 67 cm (⅔ of a meter) from the eye E for there to be sharp focussing of the respective red and blue images on the retina at F. Thus, whereas for green light the eye has a lens power of 1 dioptre, its power in respect of red light is ½ dioptre and its power in respect of blue light is 1½ dioptres. The extent of the longitudinal chromatic aberration is hence 1 dioptre, and there is evidence to suggest that the eye/brain system used this to avoid re-focussing by concentrating on the blue components of objects that are close and on the red components for more distant vision.

Referring now to FIG. 2, this shows disposed in front of the eye E an ophthalmic lens 1 which incorporates a transmission hologram 2. The hologram 2 has negative diffractive power and introduces positive longitudinal chromatic aberration which adds to the natural longitudinal chromatic aberration of the human eye explained above with reference to FIG. 1. To compensate for the negative (diffractive) lens power of the hologram 2 the lens 1 has positive refractive power which can have an absolute value the same as that of the negative diffractive power of the hologram 2 so that the powers cancel. The effect then is that the lens has an overall or residual zero lens power but still introduces positive longitudinal chromatic aberration which adds to that of the eye. Hence, as shown in FIG. 2, while a green object G at the same position as the green object G in FIG. 1 is sharply focussed on to the eye retina at F, a blue object B has to be nearer to the eye than the blue object B in FIG. 1 to achieve sharp focussing at F, and a red object R has to be further from the eye than the red object R in FIG. 1 to achieve sharp focussing at F.

As explained above with reference to FIG. 1, the extent of the natural longitudinal chromatic aberration of the eye is about 1 dioptre. If it is desired to increase this to, for example, 2 dioptres, i.e. so that in FIG. 2 the blue object B is at a distance of 50 cm from the eye and the red object R is at 4 meters or more (i.e. approximating to effectively infinite), then one dioptre of longitudinal chromatic aberration is required from the hologram 2. This can be achieved by use of a hologram with a diffractive power of −3.4 dioptres. To compensate for this the refractive power of the lens 1 then needs to be +3.4 dioptres so that the power values cancel each other.

It will be appreciated that if the eye E in fact requires some corrective power, then the refractive power of the lens 1 need not balance the diffractive power of the hologram 2, but the values could be so selected as to give an overall power or to leave a residual power which is that required by the particular eye for correction. For example, a patient with a +2 dioptre refractive error could wear a lens 1 which combines a −3.4 dioptre diffractive power hologram 2 with a refractive power of +5.4 dioptres.

If a negative power correction for the eye is required then the diffractive power of the hologram 2 could exceed the refractive power of the lens 1, and if a negative corrective power even greater than the negative diffractive power of the hologram 2 is required then the refractive power of the lens 1 could also be negative so as to add to that of the hologram 2. In the peculiar case where a patient requires a negative corrective power equal to the negative diffractive power of the hologram 2, then the lens 1 can be of zero refractive power.

It will be understood that increasing the extent of the longitudinal chromatic aberration (e.g. to 2 dioptres) can enable the eye to perform a wide variety of tasks without needing to adjust its focus (accommodate). By use of a combination of holographic (diffractive) and refractive lens elements the resultant power can be largely the same as that required for clear distance or intermediate vision, while the change of power with colour (wavelength) of light is considerably enhanced. The use of a holographic optical element enables the ophthalmic lens to be of small size and light weight; it can therefore readily and comfortably be worn by the user.

The ophthalmic lens 1 may take the form of a spectacle lens, or may be a contact lens, or could be an implant lens which is surgically inserted in the eye to replace a defective natural lens L.

In the case of a contact lens (or an implant lens) the hologram 2 would extend over the full visually used area of the lens. With a spectacle lens, the hologram 2 may be provided only over a reading portion or near portion, as in a bifocal or progressive lens.

The hologram 2 may be optically generated in or on the lens 1, or may be mechanically generated as a surface relief hologram on or in the lens 1. The hologram may take a form, and/or be generated in a manner, as described in U.S. patent application Ser. No. 368,362 filed Apr. 14, 1982, the relevant teachings of which are incorporated herein by reference.

The refractive power of the lens 1 is provided by refracting faces which are curved when viewed in axial-section (as in FIG. 2 which shows curved anterior and posterior refracting faces 3 and 4) and which may be of spherical curvature. It will be understood that any longitudinal chromatic aberration of the basic refractive lens is very small and has only a slight effect on that of the holographic element.

It will further be understood that the present invention makes particular use of change of power with colour (wavelength), and that references herein to power (whether refractive, diffractive, residual, overall, corrective, etc.) which are not qualified by colour or wavelength are to be understood as applying to green light of wavelength 555 nanometers unless the context indicates otherwise. However, it is required that the introduction of longitudinal chromatic aberration with the diffractive power should occur substantially uniformly across the full continuum of the visible spectrum and with high efficiency. A hologram 2 of as uniformly high efficiency as possible is therefore called for, e.g. an efficiency of more than 50%, and preferably at least 80%, at all wavelengths, and preferably with less than 20% difference between the maximum and minimum efficiencies, across the visible spectrum.

The maximum efficiency should preferably be greater than 70%. A particular example of hologram may have a minimum efficiency of about 85% or more at the extremes of the visible spectrum and a maximum efficiency of about 99% or higher at the centre for green light.

It has previously been mentioned that the diffractive power of the lens may be about −3.4D dioptres, where D dioptres is the extent of positive longitudinal chromatic aberration required to be introduced (−3.4 being the effective disperson or V value of diffractive optics). However, the diffractive power need not be uniform over the whole lens area. In particular, in order to overcome or reduce possible problems which may occur when the pupil is large, the magnitudes of the diffractive and refractive powers may reduce from the centre of the lens outwardly. Such centre to edge variation of both the diffractive power and the refractive power enables the chromatic aberration to be reduced for larger diameters while keeping the residual power of the lens constant over the whole diameter. Preferably the magnitudes of the diffractive and refractive powers reduce in a manner such that red light from a distant object remains at substantially the same focus over the whole visually used area of the lens. Taking red light (which comes from a distant object effectively at infinity) as the design wavelength, gives a relatively simple relationship between the reduction of the refractive and diffractive powers such that the diminishment of diffractive power can easily balance the diminishment of refractive power all the way across the lens. With, for example, green light as the design wavelength, the relationship is more complex and the balance across the full lens therefore more difficulat.

As will be understood by those skilled in the art, the centre to edge reduction of refractive power can be achieved in practice by a suitably aspherically curved refracting surface, and the centre to edge reduction of diffractive power can be achieved in practice by a surface relief hologram of suitably varying form. It will be understood, of course, that it is the absolute magnitudes of the diffractive and refractive powers which reduce from the centre to the edge of the lens, the diffractive power having a diminishing negative value and the refractive power having a diminishing positive value, the difference (if any) between the magnitudes which provides the residual power of the lens being the same from the centre to the edge.

I claim:

1. An ophthalmic lens comprising diffracting means providing negative diffractive power which introduces positive longitudinal chromatic aberration that adds to the natural longitudinal chromatic aberration of the eye and hence increases the range of the chromatic effect.

2. A lens according to claim 1 having diffractive power of about −3.4D dioptres where D dioptres is the extent of positive longitudinal chromatic aberration required to be introduced.

3. A lens according to claim 1 having refractive power.

4. A lens according to claim 3 having positive refractive power.

5. A lens according to claim 4 in which the refractive power is of a magnitude such as to balance the diffractive power.

6. A lens according to claim 3 in which the relative values of the diffractive and refractive powers are such as to provide the lens with an overall or residual power.

7. A lens according to claim 3 whose refractive power is provided by faces which are curved as viewed in axial section.

8. A lens according to claim 7 in which the curved faces are of spherical curvature.

9. A lens according to claim 3 in which the magnitudes of the diffractive and refractive powers reduce from the centre of the lens outwardly.

10. A lens according to claim 9 in which the magnitudes of the diffractive and refractive powers reduce in a manner such that red light from a distant object remains at substantially the same focus over the whole visually used area of the lens.

11. A lens according to claim 1 in which the diffractive power is provided by a transmission hologram.

12. A contact lens according to claim 1.

13. A spectacle lens according to claim 1.

14. An implant lens according to claim 1.

15. A lens according to claim 1 having an efficiency of diffraction more than 50% at all wavelengths across the visible spectrum.

16. A lens according to claim 15 having a maximum efficiency of diffraction of more than 70%.

17. A lens according to claim 15 in which the difference between the maximum and minimum efficiencies of diffraction across the visible spectrum is less than 20%.

18. An ophthalmic lens comprising diffracting means providing negative diffractive power which introduces positive longitudinal chromatic aberration that adds to the natural longitudinal chromatic aberration of the eye and hence increases the range of the vision of the eye at any one accomodation setting by increasing the spacing between a blue object at one distance and a red object at a greater distance whose images are sharply focused on the retina.

* * * * *